United States Patent
Hull et al.

(10) Patent No.: US 10,191,014 B2
(45) Date of Patent: Jan. 29, 2019

(54) SYSTEM AND METHOD FOR NONDESTRUCTIVE EVALUATION OF A TEST OBJECT

(71) Applicant: The Boeing Company, Chicago, IL (US)

(72) Inventors: John R. Hull, Sammamish, WA (US); Gary E. Georgeson, Tacoma, WA (US); Morteza Safai, Newcastle, WA (US); Barry A. Fetzer, Renton, WA (US); Steven K. Brady, Seattle, WA (US); Jeffrey G. Thompson, Auburn, WA (US)

(73) Assignee: The Boeing Company, Chicago, IL (US)

( * ) Notice: Subject to any disclaimer, the term of this patent is extended or adjusted under 35 U.S.C. 154(b) by 185 days.

(21) Appl. No.: 15/244,698

(22) Filed: Aug. 23, 2016

(65) Prior Publication Data
US 2018/0059065 A1  Mar. 1, 2018

(51) Int. Cl.
*G01N 29/04* (2006.01)
*G01S 19/13* (2010.01)
(Continued)

(52) U.S. Cl.
CPC ............ *G01N 29/2412* (2013.01); *G01J 5/10* (2013.01); *G01N 25/72* (2013.01); *G01N 29/041* (2013.01);
(Continued)

(58) Field of Classification Search
CPC ........ G01N 29/04; G01N 29/06; G01N 29/24; G01N 29/275; G01N 29/2412;
(Continued)

(56) References Cited

U.S. PATENT DOCUMENTS 4,955,236 A  9/1990  Yokoyama et al.
5,149,025 A  9/1992  Utterback et al.
(Continued)

OTHER PUBLICATIONS

Layman, Christopher N. et al.; "Characterization of acoustic streaming and heating using synchronized infrared thermography and particle image velocimetry"; Ultrasonics Sonochemistry 18 (2011); pp. 1258-1261; doi:10.1016/j.ultsonch.2011.03.012 (Mar. 30, 2011).

(Continued)

*Primary Examiner* — Helen C Kwok
(74) *Attorney, Agent, or Firm* — Vivacqua Law

(57) ABSTRACT

A system for nondestructive evaluation of a test object includes a platform, an electromagnetic acoustic transducer (EMAT) to create acoustic vibrations that travel along the test object; an infrared detector positioned to record thermal images of a plurality of test areas on the test object to detect flaws in the test object as the platform and the test object move relative to each other; and a control connected to actuate the EMAT and the infrared detector, synchronize the creation of vibrations with the recording of thermal images, receive a signal from the infrared detector indicative of the thermal image of the surface of the test object, and record locations of the flaws appearing on the thermal images of the test areas, all as the platform and the test object move relative to each other.

18 Claims, 2 Drawing Sheets

(51) Int. Cl.
  *G01J 5/10* (2006.01)
  *G01N 29/24* (2006.01)
  *G01N 25/72* (2006.01)
  *G01N 29/06* (2006.01)
  *G01N 29/275* (2006.01)
  *G01J 5/00* (2006.01)

(52) U.S. Cl.
  CPC ....... *G01N 29/048* (2013.01); *G01N 29/0618* (2013.01); *G01N 29/275* (2013.01); *G01S 19/13* (2013.01); *G01J 2005/0077* (2013.01); *G01N 2291/0231* (2013.01); *G01N 2291/0234* (2013.01); *G01N 2291/0423* (2013.01); *G01N 2291/101* (2013.01); *G01N 2291/2623* (2013.01); *G01N 2291/2694* (2013.01); *G01N 2291/2696* (2013.01)

(58) Field of Classification Search
  CPC ...... G01N 29/348; G01N 29/46; G01N 25/22; G01N 25/72; G01J 5/10
  See application file for complete search history.

(56) References Cited

U.S. PATENT DOCUMENTS

| | | | |
|---|---|---|---|
| 5,287,183 A * | 2/1994 | Thomas | H04N 5/217 348/571 |
| 5,335,995 A | 8/1994 | Villar | |
| 5,677,533 A | 10/1997 | Yaktine et al. | |
| 5,763,786 A * | 6/1998 | Camplin | G01N 29/0609 702/39 |
| 5,870,192 A * | 2/1999 | Barker | G01P 3/366 356/477 |
| 6,399,948 B1 * | 6/2002 | Thomas | G01N 25/72 250/334 |
| 6,998,616 B2 * | 2/2006 | Favro | G01N 3/60 250/341.6 |
| 7,075,084 B2 | 7/2006 | Thompson et al. | |
| 7,119,338 B2 | 10/2006 | Thompson et al. | |
| 7,295,321 B1 * | 11/2007 | Marshall | G01S 17/58 356/28.5 |
| 8,806,950 B2 * | 8/2014 | Hull | G01N 29/043 73/578 |
| 9,689,760 B2 * | 6/2017 | Lanza di Scalea | G01L 1/255 |
| 9,752,993 B1 * | 9/2017 | Thompson | G01M 17/10 |
| 2004/0159790 A1 | 8/2004 | Thompson et al. | |
| 2009/0049936 A1 | 2/2009 | Mian et al. | |
| 2010/0019153 A1 | 1/2010 | Zalameda et al. | |
| 2010/0076631 A1 * | 3/2010 | Mian | G05D 1/0229 701/19 |
| 2013/0191070 A1 | 7/2013 | Kainer et al. | |
| 2014/0316719 A1 | 10/2014 | Lanza di Scalea et al. | |
| 2015/0377836 A1 * | 12/2015 | Lanza di Scalea | G01M 5/0025 73/598 |
| 2016/0018324 A1 * | 1/2016 | Georgeson | G01N 21/171 250/341.6 |

OTHER PUBLICATIONS

EP, Extended European Search Report and Opinion; Patent Application No. 17173251.4; 9 pages (dated Oct. 27, 2017).
U.S., Notice of Allowance, U.S. Appl. No. 15/265,509; 9 pages (dated Jun. 21, 2017).

* cited by examiner

SYSTEM AND METHOD FOR NONDESTRUCTIVE EVALUATION OF A TEST OBJECT

TECHNICAL FIELD

The disclosure relates to nondestructive evaluation systems and methods and, more particularly, to systems and methods for the non-contact, nondestructive evaluation of test objects.

BACKGROUND

It is necessary to maintain the integrity of structural objects and components that have been subjected to wear and stress from use and hazards of the environment in which such objects and components operate. Accordingly, it is desirable to test such structural objects and components periodically to determine whether they have degraded in strength or reliability due to such flaws as surface cracks, corrosion, disbonds, and the like. In some instances, it is possible to remove the object to be tested from its location of use and perform a test of its integrity while it is mounted on a test stand in a laboratory using laboratory instruments. However, in many instances the test object is very large or is integrated into a larger structure in a manner that make its removal impracticable, making it difficult if not impossible to remove it for remote testing.

In addition, it is desirable to perform nondestructive evaluation (NDE) tests on objects. NDE tests do not permanently alter an object in an undesirable manner, which may render the test object useless for its intended purpose.

Nondestructive evaluation systems and methods have been developed to provide non-contact inspection of components and structures in the field to detect flaws and otherwise determine the integrity of such structures and components. For example, techniques have been developed for infrared or thermal imaging of subsurface defects in a material that are illuminated by ultrasonic or sonic vibrations. A sound source generates sound waves in the test object by pulses of energy having a constant frequency and amplitude for a predetermined period of time.

The sound source can be an electromagnetic acoustic transducer (EMAT) that provides broadband, pulsed ultrasonic energy. A thermal imaging camera or device is used to image the test object as it is being excited by the EMAT sound source. A sequence of images is recorded that may show cracks and other defects in the test material, which appear as light areas against a darker background. The images may be displayed on a monitor, and a storage device may be provided to store the sequence of images to be reviewed at a later time.

Disadvantages with such techniques for infrared or thermal imaging of subsurface defects in a material arise because of the need to fix the distance between the source of sound waves—the EMAT—and the infrared imaging device so that the propagation of sound waves in the test object may be properly synchronized between the transmitter of the sound waves and the imaging device. Further, there is a need for providing such nondestructive evaluation systems that may operate on relatively large objects and that may inspect large objects in a short amount of time.

SUMMARY

The disclosed system for nondestructive evaluation of a test object may be mounted on a platform that either moves relative to the test object, remains stationary as the test object moves, or in which both the platform and test object move, and yet accurately and continuously records thermal images of the surface of the test object to detect flaws that appear in response to vibrations. In one embodiment, a system for nondestructive evaluation of test object includes a platform, and an electromagnetic acoustic transducer (EMAT) mounted on the platform and positioned to generate a magnetic field in the test object to create acoustic vibrations that travel along a surface of the test object; an infrared detector mounted on the platform and positioned to record thermal images of a plurality of test areas on the surface test object to detect flaws in the surface of the test object within the plurality test areas as at least one of the platform and the test object move relative to each other; and a control connected to actuate the EMAT to create vibrations in the test object and to actuate the infrared detector, synchronize the creation of vibrations by the EMAT with the recording of thermal images of the plurality of test areas by the infrared detector such that the infrared detector records each of the thermal images when one of the plurality of test areas imaged by the infrared detector receives one of the acoustic vibrations from the EMAT, receive a signal from the infrared detector indicative of the thermal image of the surface of the test object, and record locations of the flaws appearing on the thermal images of the plurality test areas, all as at least one of the platform and the test object move relative to each other.

In another embodiment, a system for nondestructive evaluation of a surface of a rail may include a carriage shaped to be placed on and moved relative to the rail; an electromagnetic acoustic transducer (EMAT) mounted on the carriage and positioned to generate a magnetic field in the rail to create acoustic vibrations that travel along a surface of the rail; an infrared detector mounted on the carriage and positioned to record thermal images of a plurality of test areas on the surface of the test object as the carriage moves relative to the rail to detect flaws in the surface of the test object within the plurality of test areas; and a control connected to actuate the EMAT to create vibrations in the rail and to actuate the infrared detector, synchronize the creation of vibrations by the EMAT with the recording of thermal images of the plurality of test areas by the infrared detector such that the infrared detector records each of the thermal images when one of the plurality of test areas imaged by the infrared detector receives one of the acoustic vibrations from the EMAT, receive a signal from the infrared detector indicative of the thermal image of a surface of the rail and record locations of the flaws appearing on the thermal images of the plurality of test areas, all as the carriage moves relative to the rail.

In yet another embodiment, a method for nondestructive evaluation of a test object includes moving at least one of a platform and the test object relative to each other; and during moving, creating acoustic vibrations along a surface of the test object by actuating an electromagnetic transducer (EMAT) mounted on the platform to generate a magnetic field in the test object actuating an infrared detector mounted on the platform to record thermal images of a plurality of test areas on the surface of the test object, synchronizing actuating the EMAT with actuating the infrared detector for the plurality of test areas to record the thermal images as the acoustic vibrations reach each of the plurality of test areas to illuminate flaws in the surface of test object within each of the plurality of test areas, and recording at least one of the thermal images showing illuminated flaws appearing on one of the plurality of test areas.

Other objects and advantages of the disclosed system and method for nondestructive evaluation of a test object will be apparent from the following description, the accompanying drawings, and the appended claims.

DETAILED DESCRIPTION

Figure 1:
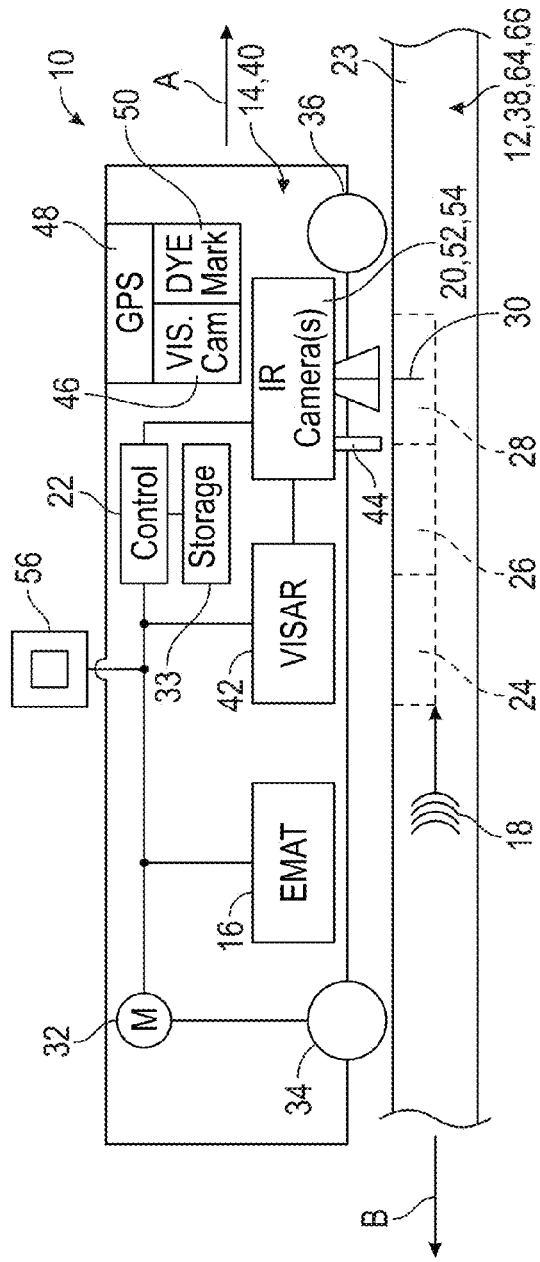
FIG. 1 is a side elevation schematic of an embodiment of the disclosed system for nondestructive evaluation of a test object.

As shown in FIG. 1, a system, generally designated 10, for nondestructive evaluation of a test object, generally designated 12, may include a platform 14, an electromagnetic acoustic transducer (EMAT) 16 mounted on the platform and positioned to generate a magnetic field in the test object to create acoustic vibrations 18 that travel along a surface of the test object, an infrared detector 20, also mounted on the platform 14, and a control 22 that may be mounted on the platform or alternately, may be remote from the platform. The control 22 may be connected to actuate the EMAT and the infrared detector 20, which may take the form of one or more infrared cameras. The control 22 also may be referred to as a controller. The vibrations 18 generated by the EMAT 16 may travel along a surface 23 of the object 12.

Figure 4:
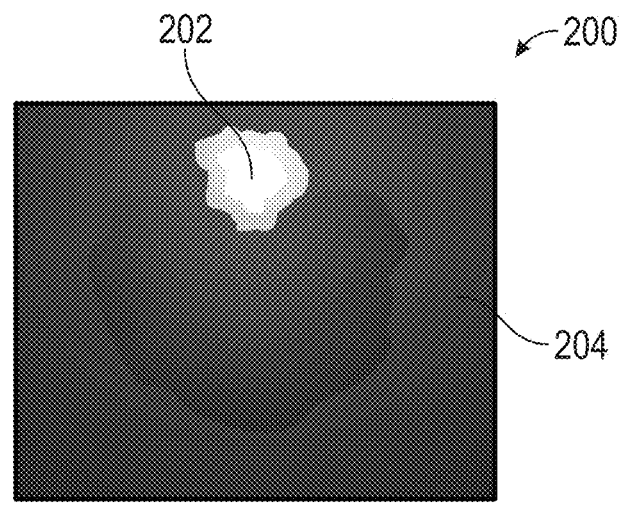
FIG. 4 is a representative thermal image showing a flaw illuminated as a bright spot.

The infrared detector 20 is positioned on the platform 14 to record thermal images, such as thermal image 200 in FIG. 4, of a plurality of test areas 24, 26, 28 on the surface 23 of the test object 12 to detect flaws, such as flaw 30 in the form of a vertical crack, within the test areas as at least one of the platform and the test object move relative to each other. In embodiments, there may be more or fewer test areas than the test areas 24, 26, 28 illustrated in FIG. 1. The test areas 24-28 may be contiguous, as shown in FIG. 1, or may be spaced from each other. In either case the test areas 24-28 may be arranged in a preset or predetermined pattern or path, which may be a linear path, on the test object 12 that may be followed by the platform 14 so that the infrared detector 20 sequentially images the test areas 24-28 making up the pattern or path. The control 22 may include storage 33 for recording thermal images taken by the infrared detector 20 as well as location information corresponding to the location of the test areas 24, 26, 28 on the test object 12.

In an embodiment, the platform 14 may include a motor 32 for moving the platform in a predetermined direction relative to the test object 12. The control 22 may be connected to the motor 32 to actuate the motor to move the platform relative to the test object 12 such that the control records a plurality of the thermal images from a plurality of contiguous images of the plurality of test areas 24, 26, 28 on the surface 23 of the test object 12 as the platform moves relative to the test object in the direction of arrow A. In embodiments, the platform 14 may move in the opposite direction of arrow A.

In an alternate embodiment, the platform 14 may remain stationary and the test object 12 may be moved relative to the stationary platform 14, for example in the direction of arrow B, or in the opposite direction of arrow B. In yet another embodiment, both the platform 14 and the test object 12 may move relative to each other, for example in the directions of arrows A and B. In embodiments in which the platform 14 is stationary relative to the test object 12, there may be no need for motor 32. In embodiments in which the platform 14 moves relative to the test object 12, the motor 32 may power a rearward wheel or pair of wheels 34 and/or a forward wheel or pair of wheels 36. In the embodiment shown in FIG. 1, the test object 12 may take the form of a rail or pair of rails 38, such as a pair of rails for a railroad or trolley system, and the platform 14 may take the form of a carriage 40 that is supported on the rails 38 by the wheels 34, 36. In such an embodiment, the motor 32 may be actuated by the control 22 to move the platform 14, which may take the form of a carriage 40, along the rails 38 at a predetermined speed for a predetermined distance. For example, in an environment in which the rails 38 are railroad rails, the maximum speed of the carriage 40 may be 25 miles per hour.

Regardless of the movement of the platform 40 relative to the test object 12, the control 22 may actuate the EMAT 16 to create the vibrations 18 in the surface 23 of the test object and to actuate the infrared detector 20, which in embodiments may take the form of one or more infrared cameras, synchronize the creation of the vibrations by the EMAT with the recording of thermal images of the plurality of test areas 24, 26, 28 by the infrared detector such that the infrared detector records each of the thermal images when one of the plurality test areas imaged by the infrared detector receives one of the acoustic vibrations from the EMAT. The control 22 also may receive a signal from the infrared detector 20 indicative of the thermal image of the surface 23 of the test object 12, and record the location of one or more flaws 30 appearing on the thermal images of the plurality of test areas 24, 26, 28, all as at least one of the platform 14 and the test object 12 move relative to each other.

In an embodiment, the system 10 may include a velocity interferometer system for any reflector (VISAR) 42 mounted on the platform 14 and connected to be actuated by the controller 22. The VISAR 42 may include a probe 44 that is oriented to detect a presence of one of the vibrations 18 in the test object 12 caused by the EMAT 16 in at least one of the plurality of test areas 24, 26, 28 aligned with the infrared detector 20. The controller 22 may be programmed to receive signals from the VISAR 42 indicating a presence of the vibrations 18 in one of the adjacent test areas 24, 26, 28 (test area 28 being shown in the figure as adjacent the infrared detector 20 and probe 24 of the VISAR 42) and actuate the infrared detector in response to record the thermal image of one of the plurality of test areas 28 aligned with the infrared detector 20.

The advantage of using the VISAR 42 is that the spacing between the EMAT 16, which generates the vibrations 18, and the infrared detector 20, need not be precise or even a known value. Rather, the infrared detector 20 is synchronized by the control 22 and triggered by the VISAR 42 upon detection of one of the vibrations 18 in the test area adjacent the infrared detector, such as test area 28 shown in FIG. 1.

It is also desirable to determine a location of a flaw, such as surface crack 30, in the test object 12. This location function may be accomplished by providing a visual camera 46 on the platform 14 and connected to the control 22. The control 22 may actuate the visual camera to digitally photograph the flaw 30 detected by the infrared detector 20. In addition to providing location information of the flaw 30, the visual camera 46 also may detect a false positive generated by the infrared detector 20. In further embodiments, the test object 12 depicted in FIG. 1 may take the form of an aircraft stringer 64 or an aircraft spar 66. With embodiments in which the test object 12 is either an aircraft stringer 64 or an aircraft spar 66, the platform 14 may be moved relative to the test object 12, but not necessarily be mounted on it for movement.

In other embodiments, location components such as a global positioning satellite sensor (GPS) 48 may be included and mounted on the platform 14. The GPS 48 may enable the control 22 to determine and record a location of flaws, such as flaw 30, detected by the infrared detector 20. In another embodiment, the system 10 may include a dye marker 50 that may be connected to be actuated by the control 22 such that upon locating a flaw 30, the die marker marks the test object 12 by applying a dye that is visible to the test object in the test area 28 of the flaw 30. Information regarding the location of flaws 30 may be kept in a data store 32 that may be accessed by the control 22 or by a remote system (not shown).

In an embodiment, the infrared detector 20 may take the form of first and second infrared cameras 52, 54, respectively. The first and second infrared cameras 52, 54, respectively, may be actuated sequentially and alternately by the control 22 such that the second infrared camera 54 records a thermal image of a second one of the plurality of test areas, for example test area 28, while the first infrared camera 52 may be transmitting a previously recorded thermal image of a first one of the plurality of test areas to the control, for example test area 26. In an embodiment, the control 22 may be programmed to actuate the first infrared camera 52 and the second infrared camera 54 such that the first one 26 of the plurality of test areas is contiguous to the second one 28 of the plurality of test areas. This process of alternately photographing test areas with two cameras 52, 54, may be repeated for an entire test object 12 with a plurality of contiguous test areas 24, 26, 28, that is, test areas that are immediately adjacent each other and are touching.

In an embodiment, the system 10 may include a display 56 that is connected either by a cable or wirelessly, to the control 22. The display 56 may show the images taken by the infrared detector 20, such as image 200 in FIG. 4. The detector 20 may take the form of the infrared cameras 52, 54, and/or the visible light camera 46, to view flaws 30 found in the test areas 24, 26, 28. An operator viewing the display 56 may cause the control 22 to actuate the dye marker 50 to mark a location on the test object 12 to denote a location of a flaw 30, which may appear on the thermal image 200 as a bright spot 202 against a relatively darker or black background 204.

Figure 2:
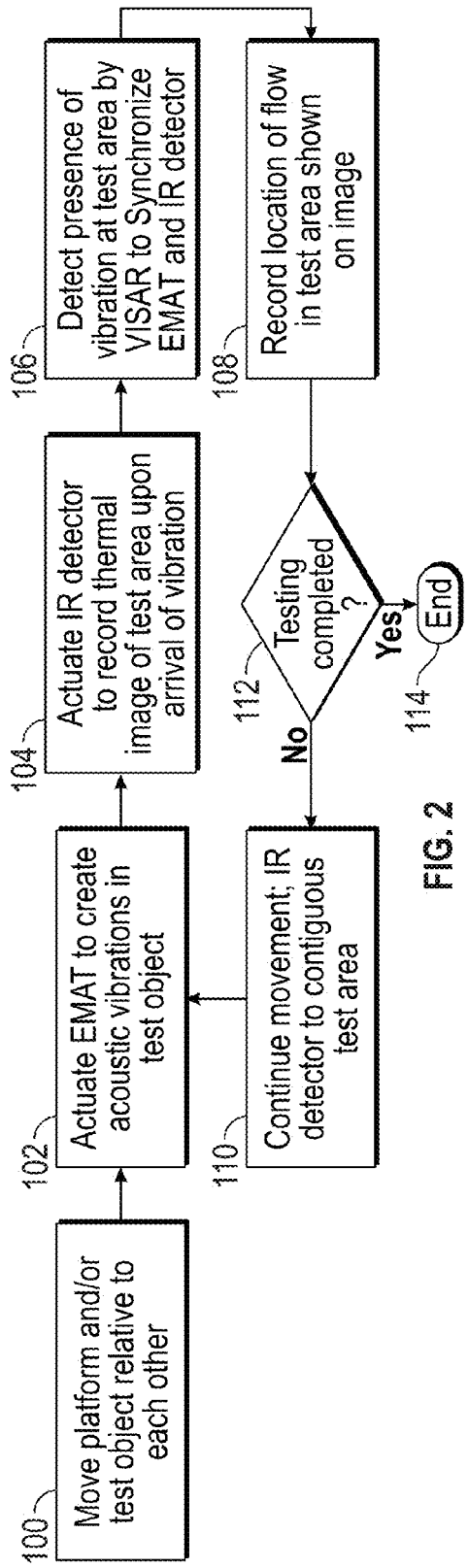
FIG. 2 is a flowchart illustrating an embodiment of the method for nondestructive evaluation of a test object.

As shown in FIG. 2, the method of nondestructive evaluation of a test object performed by the system 10 of FIG. 1 may begin with moving at least one of the platform 14 and/or the test object 12 relative to each other, as indicated in block 100. While the aforementioned relative motion is occurring, the control 22 may actuate the EMAT 16 to create acoustic vibrations along the surface 23 of the test object 12 to generate a magnetic field in the test object that creates vibrations 18, as indicated in block 102.

The control 22 may actuate the infrared detector 20, mounted on the platform 14, to record thermal images, such as thermal image 200 in FIG. 4, of a plurality of test areas 24, 26, 28 on the surface 23 of the test object 12, as indicated in block 104. In an embodiment, the presence of a vibration is detected in the test area 28 by the VISAR 42, and the controller 22 may synchronize actuating the infrared detector 20 with actuation of the EMAT 16 for the test area 28, as indicated in block 106. The EMAT 16 generates eddy currents on and just beneath the surface 23 of the test object 12. The eddy currents interact with a static magnetic field generated by the EMAT 16 in the test object 12, which generates acoustic vibrations 18 of various polarizations that may be reflected off of discontinuities in the test object. The acoustic vibrations 18 may generate heat at the defect site (e.g., flaw 30), which may appear as the bright spot 202 against a darker or black background 204 on the thermal image 200 taken by infrared detector 20.

As indicated in block 108, the control 22 may record the location of a flaw, for example flaw 30 in FIG. 1, in the respective area 28 that may be shown on the thermal image 200 obtained by the infrared detector 20. The process continues for each successive test area encountered by the platform 14 as it moves relative to the test object 12, as indicated in block 110. If the testing is complete, as indicated in block 112, the process ends as indicated in block 114. In embodiments, the step of determining a location of at least one of the thermal images of one of the test areas 28 may be effected by one or more of storing GPS coordinates associated with the thermal images, photographing the location of the thermal images with a visible light camera 46, and/or marking the location of the thermal image with a dye marker 50 on the test area 28, as is included in block 108. In embodiments, the recording and storage in storage 33 of thermal images obtained by the infrared detector 20 may be effected for each thermal image taken of the test object 12. In the alternative, only those thermal images indicating a flaw 30 may be stored in storage 33 by the control 22, as is incorporated in block 108.

Figure 3:
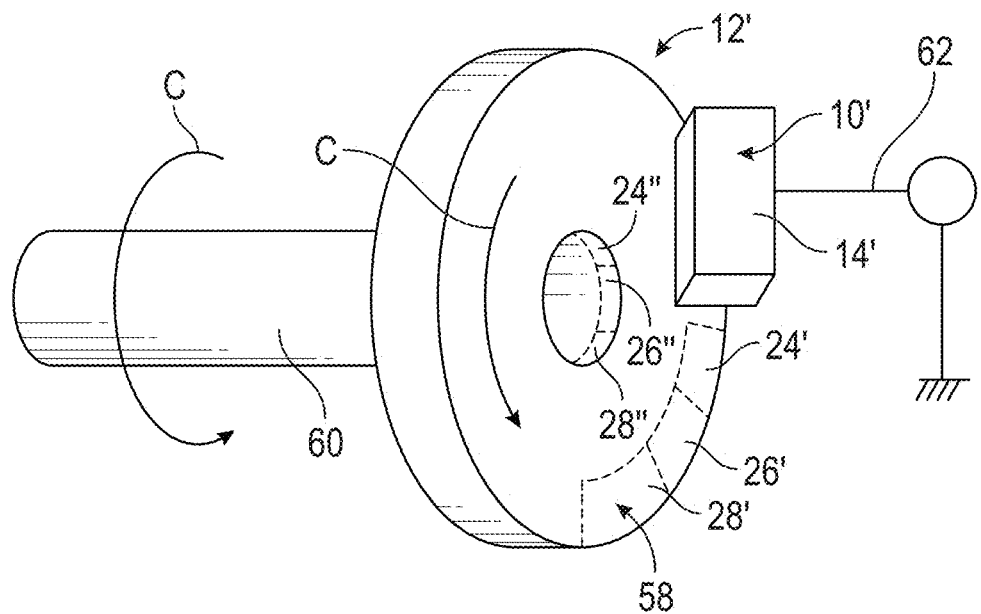
FIG. 3 is a schematic of another embodiment of the disclosed system for nondestructive evaluation of a test object.

The method depicted in FIG. 2 may be performed for the nondestructive evaluation of a test object 12 may take the form of a rail or pair of rails 38 as shown in FIG. 1. Alternately, the test object 12' may take the form of a wheel 58, as shown in FIG. 3, and/or an axle 60. In the case of a wheel 58 or axle 60, the system 10' may be stationary, and mounted on an articulated arm 62 such that the wheel 58 and/or axle 60 rotates, for example in the direction of arrow C, relative to the platform 14' (which may include the EMAT 16, VISAR 42, infrared detector 20, control 22, storage 33, visible light camera 46, dye marker 50, and GPS 48 of platform 14 of FIG. 1).

In another embodiment, the articulated arm 62 may be a robot arm that moves the platform 14' relative to the wheel 58 and/or axle 60. In either case, the platform 14' passes over test areas 24', 26', 28' on the wheel 58, and/or test areas 24", 26", 28" on the axle 60, to take thermal images, such as thermal image 200 in FIG. 4, by way of the infrared detector 20 (FIG. 1) mounted on the platform 14'.

Alternately, the platform 14 may take the form of a robot crawler, or serve as the end effector of an articulated arm, such as arm 62 depicted in FIG. 3. As indicated in FIG. 3, in embodiments, the test areas 24', 26', 28' may be arranged to be contiguous with each other, as well as test areas 24", 26", 28". With such embodiments, the method step of actuating the infrared detector indicated in block 104 of FIG. 2 may include actuating the infrared detector to record thermal images of a plurality of contiguous test areas 24-28 along a predetermined path formed by the test areas on the test object 12 (FIG. 1).

The method depicted in FIG. 2 also may include in block 108 a step of taking an image of the plurality of test areas having a flaw with a visible light camera 46 (FIG. 1), storing the image in storage 33, and comparing the image of the flaw with a visible light camera to detect a false positive which may be displayed on a split screen of display 56.

In an embodiment of the method depicted in FIG. 2, the step of synchronizing the EMAT 16 with the infrared detector 20, indicated in block 104, may include actuating first and second infrared cameras 52, 54, respectively, by the control 22, such that the second infrared camera records a thermal image of a second one of the plurality of test regions 28, while the first infrared camera is transmitting a previously recorded image of a first one of the plurality of test regions 26 to the control 22 (FIG. 1). Also included in block 104 of FIG. 2, in an embodiment, the control 22 may actuate the first infrared detector 52 and the second infrared detector 54 such that the first one of the plurality of test areas 26 is contiguous to the second one of the test areas 28.

The systems 10, 10' described with reference to FIGS. 1 and 3, and the method described with reference to FIG. 2 provide a system and method for nondestructive evaluation of a test object 12 in which detection of surface flaws 30, which may take the form of surface cracks, disbonds, corrosion, and flaws resulting from broken fibers, such as carbon fiber reinforced plastic (CFRP), and lightning strikes, may be detected and recorded in a rapid manner on a test object 12 that is in the field, and the test object need not be disconnected a larger structure or otherwise removed from its location and orientation of use. The systems 10, 10' and method described herein enable the detection of flaws 30 by a platform 14, which may be a carriage 40 that is movably mounted on the test object 12, which may be a rail or rails 38, to detect and record flaws 30 as the carriage or platform moves relative to the test object.

This relative movement may take the form of a moving carriage 40 relative to a stationary test object 12, a moving test object such as a wheel 58 or axle 60 relative to a stationary platform 14', or an embodiment in which both the test object 12 and platform 14 are moving. Further, it is not necessary to determine with precision the spacing between the EMAT 16 and the infrared detector 20 in order to synchronize the taking of thermal images with the arrival of vibrations in the test regions 24-28, because the system includes a VISAR 42 that detects the presence of a vibration in the test area and the controller 22 actuates the infrared detector 20 in response. Accordingly, the system and method for nondestructive evaluation of a test object described herein is robust, accurate, and may be utilized in a variety of environments on either stationary or moving test objects.

While the forms of apparatus methods herein described constitute preferred embodiments of the disclosed system and method for nondestructive evaluation of a test object, it is to be understood that the disclosure is not limited to these precise forms of apparatus and methods, and that changes may be made therein without departing from the scope of the disclosure.

What is claimed is:

1. A system for nondestructive evaluation of a test object, the system comprising:
   a platform;
   an electromagnetic acoustic transducer (EMAT) mounted on the platform and positioned to generate a magnetic field in the test object to create acoustic vibrations that travel along a surface of the test object;
   an infrared detector mounted on the platform and positioned to record thermal images of a plurality of test areas on the surface of the test object to detect flaws in the surface of the test object within the plurality of test areas as at least one of the platform and the test object move relative to each other;
   a velocity interferometer system for any reflector (VISAR) mounted on the platform and oriented to detect a presence of one of the vibrations in the test object caused by the EMAT in one of the plurality of test areas aligned with the infrared detector; and
   a controller connected to the EMAT, the VISAR, and the infrared detector, wherein the controller actuates the EMAT to create the vibrations in the test object the VISCAR, and the infrared detector, wherein the connection synchronizes the creation of the vibrations by the EMAT with the recording of the thermal images of the plurality of test areas by the infrared detector, wherein the controller receives signals from the VISAR indicating the presence of the vibrations in the one of the plurality of test areas aligned with the infrared detector, and the infrared detector is triggered to record each of the thermal images of the one of the plurality of test areas aligned with the infrared detector in response to the VISCAR detecting the one of the vibrations in the one of the plurality of test areas, wherein the controller receives a signal from the infrared detector indicative of the thermal images of the surface of the test object, and the controller records locations of the flaws appearing on the thermal images of the plurality of test areas, wherein the controller receives and records as at least one of the platform and the test object move relative to each other.

2. The system of claim 1, wherein the platform includes a motor for moving the platform in a predetermined direction relative to the test object; and the controller actuates the motor to move the platform relative to the test object such that the controller records a plurality of the thermal images from a plurality of contiguous images of the plurality of test areas on the test object as the platform moves relative to the test object.

3. The system of claim 1, wherein the VISAR is actuated by the controller to detect an arrival of one of the vibrations generated by the EMAT in the one of the plurality of test areas aligned with the infrared detector; and the controller actuates the infrared detector to detect the thermal images of the test object upon arrival of the one of the vibrations.

4. The system of claim 1, further comprising a visual camera mounted on the platform and connected to the controller to be actuated to photograph the flaws detected by the infrared detector.

5. The system of claim 1, wherein the controller includes a global positioning satellite (GPS) sensor that enables the controller to determine and record a location of the flaws detected by the infrared detector.

6. The system of claim 1, further including a data store connected to the controller for storing the images of the flaws detected by the infrared detector.

7. The system of claim 1, further comprising a marker that is actuated by the controller to apply a dye to a selected one of the plurality of test areas.

8. The system of claim 1, wherein the infrared detector includes first and second infrared cameras; and wherein the first and second infrared cameras are actuated sequentially by the controller such that the second infrared camera records a thermal image of a second one of the plurality of test areas, while the first infrared camera is transmitting a previously recorded image of a first one of the plurality of test areas to the controller.

9. The system of claim 8, wherein the controller actuates the first infrared camera and the second infrared camera such that the first one of the plurality of test areas is contiguous to the second one of the plurality of test areas.

10. A system for nondestructive evaluation of a surface of a rail, the system comprising:

a carriage shaped to be placed on and move relative to the rail;

an electromagnetic acoustic transducer (EMAT) mounted on the carriage and positioned to generate a magnetic field in the rail to create acoustic vibrations that travel along a surface of the rail;

an infrared detector mounted on the carriage and positioned to record thermal images of a plurality of test areas on the surface of the rail as the carriage moves relative to the rail to detect flaws in the surface of the rail within the plurality of test areas;

a velocity interferometer system for any reflector (VISAR) mounted on the platform and oriented to detect a presence of one of the vibrations in the rail caused by the EMAT in one of the plurality of test areas aligned with the infrared detector; and a controller connected to the EMAT, the VISAR, and the infrared detector, wherein the controller actuates the EMAT to create the vibrations in the rail and the controller actuates the VISAR and the infrared detector, wherein the connection synchronizes the creation of the vibrations by the EMAT with the recording of the thermal images of the plurality of test areas by the infrared detector, wherein the controller receives signals from the VISAR indicating the presence of the vibrations in the one of the plurality of test areas aligned with the infrared detector, and the infrared detector is triggered to record each of the thermal images of the one of the plurality of test areas aligned with the infrared detector in response to the VISCAR detecting the one of the vibrations in the one of the plurality of test areas, wherein the controller receives a signal from the infrared detector indicative of the thermal images of the surface of the rail, and the controller records locations of the flaws appearing on the thermal images of the plurality of test areas, wherein the controller receives and records as the carriage moves relative to the rail.

11. A method for nondestructive evaluation of a test object, the method comprising:

moving at least one of a platform and the test object relative to each other; and during the moving, creating acoustic vibrations along a surface of the test object by actuating an electromagnetic acoustic transducer (EMAT) mounted on the platform to generate a magnetic field in the test object, actuating an infrared detector mounted on the platform to record thermal images of a plurality of test areas on the surface of the test object, synchronizing the actuating of the EMAT with the actuating of the infrared detector for the plurality of test areas to record the thermal images as the vibrations reach each of the plurality of test areas to illuminate flaws in the surface of the test object within each of the plurality of test areas, wherein the synchronizing the actuating of the EMAT with the actuating of the infrared detector includes detecting the vibrations in the test object caused by the EMAT by a velocity interferometer system for any reflector (VISAR) mounted on the platform, triggering the infrared detector to record each of the thermal images of the one of the plurality of test areas aligned with the infrared detector in response to the VISCAR detecting a presence of one of the vibrations in the one of the plurality of test areas, and recording at least one of the thermal images showing the illuminated flaws appearing on one of the plurality of test areas.

12. The method of claim 11, further comprising determining a location of at least one of the thermal images of one of the plurality of test areas by one or more of storing global positioning satellite (GPS) coordinates associated with the at least one of the thermal images, photographing the location of the at least one of the thermal images with a visible light camera, and/or marking the location of the at least one of the thermal images with a dye marker on a corresponding one of the plurality of test areas.

13. The method of claim 12, wherein the determining the location of at least one of the thermal images is performed for one of the thermal images when a flaw appears on the one of the thermal images.

14. The method of claim 11, further comprising the nondestructive evaluation of the test object selected from a rail, a wheel, an axle, an aircraft stringer, and an aircraft spar.

15. The method of claim 11, wherein the actuating the infrared detector for the plurality of test areas to record the thermal images includes actuating the infrared detector to record the thermal images of a plurality of contiguous test areas along a predetermined path on the test object.

16. The method of claim 11, further comprising taking an image of one of the plurality of test areas having a flaw with a visible light camera; storing the image; and comparing the image of the flaw with a visible light camera with the image of the flaw with the infrared detector to detect a false positive.

17. The method of claim 11, wherein the synchronizing the EMAT with the infrared detector includes actuating first and second infrared cameras sequentially by a controller such that the second infrared camera records a thermal image of a second one of the plurality of test areas while the first infrared camera is transmitting a previously recorded image of a first one of the plurality of test areas to the controller.

18. The method of claim 17, wherein the controller actuates the first infrared camera and the second infrared camera such that the first one of the plurality of test areas is contiguous to the second one of the plurality of test areas.

* * * * *